(12) United States Patent
Renzi

(10) Patent No.: US 7,311,882 B1
(45) Date of Patent: *Dec. 25, 2007

(54) CAPILLARY INTERCONNECT DEVICE

(75) Inventor: Ronald F. Renzi, Tracy, CA (US)

(73) Assignee: Sandia National Laboratories, Livermore, CA (US)

(*) Notice: Subject to any disclaimer, the term of this patent is extended or adjusted under 35 U.S.C. 154(b) by 896 days.

This patent is subject to a terminal disclaimer.

(21) Appl. No.: 10/350,541

(22) Filed: Jan. 24, 2003

(51) Int. Cl.
*B01L 11/00* (2006.01)

(52) U.S. Cl. ............... 422/103; 422/100; 422/104; 285/120.1; 285/124.1; 285/124.2; 285/124.4

(58) Field of Classification Search ............ 422/99, 422/101, 103, 104; 285/120.1, 121.1, 123.1, 285/123.2, 124.1, 124.2, 124.4
See application file for complete search history.

(56) References Cited

U.S. PATENT DOCUMENTS

| | | | |
|---|---|---|---|
| 3,677,577 A | 7/1972 | Krauer et al. ............... 285/137 |
| 4,089,549 A | 5/1978 | Vyse et al. .................. 285/137 |
| 4,626,005 A * | 12/1986 | Stifter ..................... 285/124.4 |
| 4,915,419 A | 4/1990 | Smith, III .................. 285/305 |
| 4,995,646 A | 2/1991 | Johnston et al. ............ 285/137 |
| 5,209,525 A | 5/1993 | Ito .............................. 285/137 |
| 5,366,620 A | 11/1994 | Schick ........................ 210/198 |
| 5,419,208 A | 5/1995 | Schick ...................... 73/863.73 |
| 5,472,598 A | 12/1995 | Schick ........................ 210/198 |
| 5,478,119 A * | 12/1995 | Dye ............................. 285/26 |
| 5,482,628 A | 1/1996 | Schick ........................ 210/198 |
| 5,487,569 A | 1/1996 | Silvis et al. .................. 285/24 |
| 5,494,641 A | 2/1996 | Krstanovic ................. 422/103 |
| 5,534,152 A | 7/1996 | Schick ........................ 210/656 |
| 5,540,464 A | 7/1996 | Picha .......................... 285/328 |
| 5,644,395 A | 7/1997 | Folta .......................... 356/246 |
| 5,736,036 A | 4/1998 | Upchurch et al. .......... 210/198 |
| 5,833,278 A * | 11/1998 | Rianda et al. ............. 285/124.1 |
| 5,846,396 A | 12/1998 | Zanzucchi et al. .......... 204/601 |
| 5,855,229 A | 1/1999 | Gluf, Jr. ..................... 137/884 |
| 5,865,474 A | 2/1999 | Takahashi ................ 285/124.1 |
| 5,987,735 A | 11/1999 | Horning et al. ............... 29/737 |

(Continued)

OTHER PUBLICATIONS

U.S. Appl. No. 10/351,714, filed Jan. 27, 2003, Renzi.

(Continued)

*Primary Examiner*—Jill Warden
*Assistant Examiner*—Dwayne K. Handy
(74) *Attorney, Agent, or Firm*—Cascio Schmoyer & Zervas

(57) ABSTRACT

A manifold for connecting external capillaries to the inlet and/or outlet ports of a microfluidic device for high pressure applications is provided. The fluid connector for coupling at least one fluid conduit to a corresponding port of a substrate that includes: (i) a manifold comprising one or more channels extending therethrough wherein each channel is at least partially threaded, (ii) one or more threaded ferrules each defining a bore extending therethrough with each ferrule supporting a fluid conduit wherein each ferrule is threaded into a channel of the manifold, (iii) a substrate having one or more ports on its upper surface wherein the substrate is positioned below the manifold so that the one or more ports is aligned with the one or more channels of the manifold, and (iv) means for applying an axial compressive force to the substrate to couple the one or more ports of the substrate to a corresponding proximal end of a fluid conduit.

26 Claims, 5 Drawing Sheets

U.S. PATENT DOCUMENTS

| | | | | |
|---|---|---|---|---|
| 5,988,703 | A | 11/1999 | Craig | 285/288.1 |
| 6,083,763 | A | 7/2000 | Balch | 436/518 |
| 6,086,825 | A | 7/2000 | Sundberg et al. | 422/100 |
| 6,090,251 | A | 7/2000 | Sundberg et al. | 204/453 |
| 6,102,449 | A | 8/2000 | Welsh | 285/342 |
| 6,102,987 | A | 8/2000 | Lang | 604/246 |
| 6,129,331 | A | 10/2000 | Henning et al. | 251/11 |
| 6,190,616 | B1 | 2/2001 | Jovanovich et al. | 422/103 |
| 6,224,728 | B1 | 5/2001 | Oborny et al. | 204/450 |
| 6,267,143 | B1 | 7/2001 | Schick | 137/625.11 |
| 6,293,725 | B1 | 9/2001 | Winkvist | 403/282 |
| 6,312,960 | B1 | 11/2001 | Balch et al. | 436/518 |
| 6,319,476 | B1 | 11/2001 | Victor, Jr. et al. | 422/103 |
| 6,344,145 | B1 | 2/2002 | Garguilo et al. | 210/635 |
| 6,358,387 | B1 | 3/2002 | Kopf-Sill et al. | 204/603 |
| 6,585,296 | B1 * | 7/2003 | Picha et al. | 285/124.1 |
| 6,832,787 | B1 * | 12/2004 | Renzi | 285/124.1 |
| 6,926,313 | B1 * | 8/2005 | Renzi | 285/353 |
| 6,966,336 | B1 * | 11/2005 | Renzi | 137/625.18 |
| 7,014,222 | B1 * | 3/2006 | Poppe | 285/332.1 |
| 2001/0045235 | A1 | 11/2001 | Schick | |

OTHER PUBLICATIONS

U.S. Appl. No. 10/350,626, filed Jan. 24, 2003, Renzi.
U.S. Appl. No. 10/405,204, filed Apr. 2, 2003, Renzi.
U.S. Appl. No. 10/405,842, filed Jan. 24, 2003, Renzi et al.
U.S. Appl. No. 10/350,628, filed Jan. 24, 2003, Renzi.
Catalog of Chromatography & Fluid Transfer Fittings, Upchurch Scientific, 2000, pp. 1, 8, 16, 20, and 22-23.
Catalog of Chromatography & Fluid Transfer Fittings, Upchurch Scientific, 2002, pp. 21 and 24.
Products for Chromatography and Fluid/Gas Transfer, VICI Jour Research, Mar. 2002, pp. 30-31.

* cited by examiner

CAPILLARY INTERCONNECT DEVICE

This invention was made with Government support under Contract No. DE-AC04-94AL85000 awarded by the U.S. Department of Energy to Sandia Corporation. The Government has certain rights to the invention.

FIELD OF THE INVENTION

The present invention relates generally to microfluidic systems and more particularly to structures which facilitate the introduction of fluids into devices having microfluidic channels.

BACKGROUND OF THE INVENTION

Microfluidic devices or substrates typically consist of two or more microchannels or capillaries that can range in size from about 5-100 µm wide and 5-100 µm deep etched or molded in a substrate that can be silicon, plastic, quartz, glass, or plastic. Microfluidic substrates may be fabricated using photolithographic techniques similar to those used in the semi-conductor industry, and the resulting devices can be used to perform a variety of sophisticated chemical and biological analytical techniques. Microfluidic analytical technology has a number of advantages, including the ability to use very small sample sizes, typically on the order of nanoliters. The substrates may be produced at a relatively low cost, and can be formatted to perform numerous specific analytical operations, including mixing, dispensing, valving, reactions, and detections.

Another recently developed class of sample-receiving microfluidic substrates includes substrates having a capillary interface that allows compounds to be brought onto the test substrate from an external source, and which can be advantageously used in a number of assay formats for high-throughput screening applications. These assay formats include fluorogenic assays, fluorescence polarization assays, non-fluorogenic mobility shift assays, dose response assays, and calcium flux cell-based assays.

Other applications for microfluidic devices include diagnostics involving biomolecules and other analytical techniques such as micro total analysis systems. Such devices, often referred to in the art as "microchips," also may be fabricated from plastic, with the channels being etched, machined or injection molded into individual substrates. Multiple substrates may be suitably arranged and laminated to construct a microchip of desired function and geometry. In all cases, the channels used to carry out the analyses typically are of capillary scale dimension.

To fully exploit the technological advances offered by the use of microfluidic devices and to maintain the degree of sensitivity for analytical techniques when processing small volumes, e.g., microliters or less, connectors which introduce and/or withdraw fluids, i.e., liquids and gases, from the device, as well as interconnect microfluidic devices, are crucial components in the use and performance of the microfluidic device. For example, chromatographic applications require an injection port that can introduce a sample into a flow stream. The varied uses of these microfluidic devices require connectors that are both versatile and resilient. The physical stresses placed on these connectors can be demanding. Not only must the connectors be inert to reactive substances that are injected into the microchannels, such as organic solvents, but also they must remain leak free when exposed to pressures that can reach as high as 10,000 psi. Moreover, these connectors must be able to act as an interface for connecting macroscale devices such as injectors and fluid reservoirs to microscale capillary tubes. However, because of the extremely small tolerances involved this has been difficult to achieve. Typically, capillary tubes have outer diameters on the order of 150 to 365 µm and nominal internal diameters of from 50 to 75 µm or less with tolerances as small as a few microns, yet these capillary tubes must be accurately aligned.

A common technique used in the past involves bonding a length of tubing to a port on the microfluidic device with epoxy or other suitable adhesive. Adhesive bonding is unsuitable for many chemical analysis applications because the solvents used attack the adhesive which can lead to channel clogging, detachment of the tubing, and/or contamination of the sample and/or reagents in or delivered to the device. Furthermore, adhesive bonding results in a permanent attachment of the tubing to the microfluidic device which makes it difficult to change components, i.e., either the microfluidic device or the tubing, if necessary. Thus assembly, repair and maintenance of such devices become labor and time intensive, a particularly undesirable feature when the microfluidic device is used for high throughput screening of samples such as in drug discovery.

To avoid problems associated with adhesive bonding, other techniques have been proposed, e.g., press fitting the tubing into a port on the microfluidic device. However, such a connection typically is unsuitable for high-pressure applications such as HPLC. Additionally, pressing the tubing into a port creates high stress loads on the microfluidic device which could lead to fractures of the channels and/or device.

Other methods involved introducing liquids into an open port on the microfluidic device with the use of an external delivery system such as a pipette. However, this technique also is undesirable due to the possibility of leaks and spills which may lead to contamination. In addition, the fluid is delivered discretely rather than continuously. Moreover, the use of open pipetting techniques does not permit the use of elevated pressure for fluid delivery such as delivered by a pump, thereby further restricting the applicability of the microfluidic device.

Microfluidic devices generally comprise an array of micron-sized wells or reservoirs and interconnecting channels disposed on a substrate. The wells are connected to distribution means for dispensing fluids to and collecting fluids from the array. Connection to the wells is typically by means of a micropipette end. While this serves for benign addition of fluids this means of fluid addition cannot be used for those applications where the access ports are exposed to a pressure differential or where it is desired to connect capillary tubes to fluid wells.

Typically, in microscale devices the microchannels are terminated by ports or wells that provide access to the microchannels. Materials are added to the microchannels through these ports or wells. Access to the ports is typically by means of a micropipette end. While this serves for benign addition fluids it cannot be used for those applications where the access ports are exposed to a pressure differential or adverse environments.

Therefore, a need exists for an improved microfluidic connector which is useful with all types of microfluidic devices and which provides an effective, high pressure connector with low fluid dead volume seal. In general, the connector should be able to connect a first set of capillaries to a second set of capillaries. The first set can be external capillaries whereas the second set can be from a microfluidic device.

SUMMARY OF THE INVENTION

The invention is based in part on the development of an interconnecting device for connecting a plurality of first fluid-bearing conduits to a corresponding plurality of second fluid-bearing conduits thereby providing fluid communication between the first fluid-bearing conduits and the second fluid-bearing conduits. In one embodiment the connector includes:

a support plate;

a manifold that is positioned on the support plate and that defines a plurality of recess regions within the manifold and having a plurality of channels wherein each channel has a first opening at a lower end of each recess region and a second opening at a lower surface of the manifold, wherein each of the second fluid-bearing conduits is positioned within one of the channels so that the distal end of each second fluid-bearing conduit is positioned in or near the first opening;

a ferrule plate that is positioned on the manifold and that defines a plurality of protrusions wherein each protrusion fits into a corresponding recess region of the manifold and the ferrule plate has a plurality of passages with each passage traversing the height of the ferrule plate and through the protrusion and wherein each of the first fluid-bearing conduits is positioned within one of the passages so that the proximal end of each first fluid-bearing conduit abuts the distal end of a corresponding second fluid-bearing conduit; and means for applying an axial force on the ferrule plate to cause the plurality of protrusions of the ferrule plate to contact a corresponding recess region of the manifold.

In another embodiment, the connector includes:

a support plate;

a lower ferrule plate that is positioned on the support plate and that defines a plurality of first protrusions;

a manifold that is positioned on the lower ferrule plate and that defines (i) a plurality of first recess regions within the manifold and (ii) a plurality of second recess regions within the manifold, wherein each of the first recess regions is connected to a corresponding second recess region;

an upper ferrule plate that is positioned on the manifold and that defines a plurality of second protrusions wherein each second protrusion fits into a corresponding second recess region and wherein the upper ferrule plate has a plurality of second passages with each second passage traversing the height of the upper ferrule plate and through the second protrusions, and wherein each first protrusion of the first ferrule plate fits into a corresponding first recess region so that each first passage of the lower ferrule plate is in communication with a corresponding second passage of the upper ferrule plate and wherein each of the first fluid-bearing conduits is positioned within one of first passages and each of the second fluid-bearing conduits is positioned within one of the second passages so that that the proximal end of each first fluid-bearing conduit abuts the distal end of a corresponding second fluid-bearing conduit; and means for applying an axial force on the first and second ferrule plates to cause the plurality first protrusions to contact a corresponding first recess region and to cause the plurality second protrusions to contact a corresponding second recess regions.

The connector is particularly suited for connecting two sets of capillaries but the connector device can also accommodate ferrules and vials. In use, the connector device can be positioned on the surface of a microscale device so that the ports of the microscale device is in fluid communication with the connector.

DESCRIPTION OF THE PREFERRED EMBODIMENTS

The invention is directed to techniques for connecting two sets of capillaries together and for connecting capillaries and/or other fluid conduits directly to inlet and/or outlet ports of a microscale device. For convenience, one set will be referred to as the "inlet" capillaries and the other set as the "outlet" capillaries. It is not intended that the structures and dimensions of the inlet and outlet capillaries be different. Preferred capillaries have circular inner diameters that range from 5 microns to 250 microns. Capillaries are available commercially from numerous sources including, for example, Polymicro Technologies LLC (Phoenix, Ariz.).

The inventive interconnecting device is particularly suited for connecting inlet capillaries to outlet capillaries that are in turn connected to a microfluidic substrate or device. The outlet capillaries, for example, may be connected to sources of chemicals, solvents and other fluids that are delivered to and used in the microfluidic device. Alternatively, some or all of the outlet capillaries may be connected to waste containers, other microfluidic devices, and/or other external bodies where fluids are sent.

The interconnect device is particularly suited for high pressure operations where the internal, i.e., liquid fluid, pressures within the capillaries are at least 500 psi. It has been demonstrated that the inventive interconnect device will withstand pressures of up to at least 5,000 psi.

Figure 1:
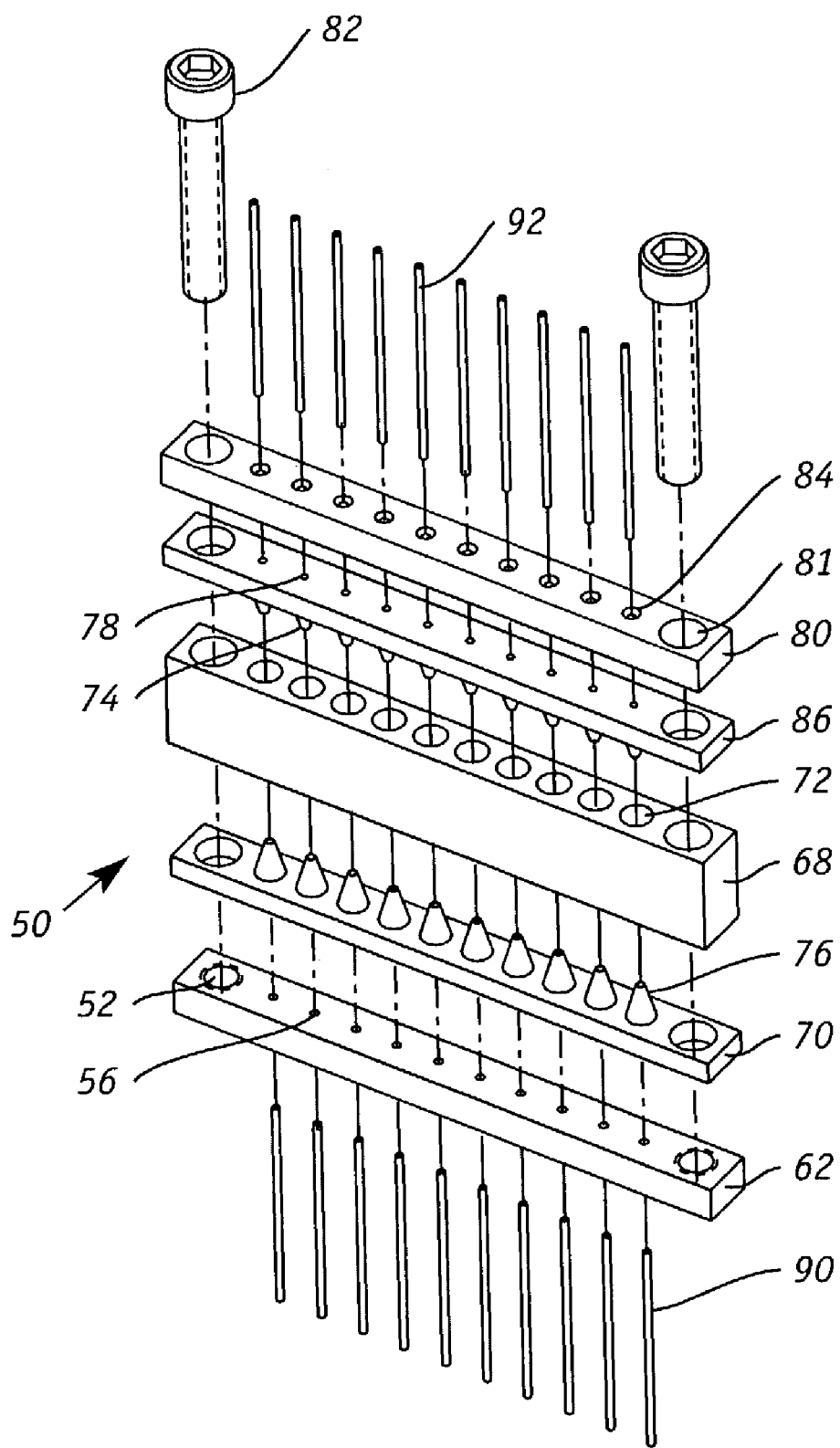
FIG. 1 is a perspective view of a disassembled capillary interconnect device.
Figure 2:
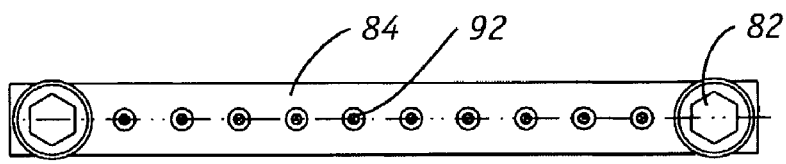
FIG. 2 is a top view of the device as assembled.

FIGS. 1-4 illustrate one embodiment of the capillary interconnect device. As depicted in FIG. 1, the device 50 includes (i) a lower interconnect stiffening or support plate 62; (ii) lower ferrule plate 70; (iii) manifold 68; (iv) upper ferrule plate 86; and (v) top interconnect plate 80. The support plate 62 and top interconnect plate 80 ensure uniform sealing of device 50 as described further herein. Support plate 62 is provided with threaded wells 52 at both ends that receive screws 82 that hold the various parts of the capillary interconnect device 50 in proper orientation and fasten the parts of the device together. Support plate 62 has a linear array of apertures 56 through which capillaries 90 are inserted as described further herein. Both support plate 62 and top interconnect plate 80 are preferably made of a stiff material such as metal, e.g., stainless steel, or high strength ceramics.

Manifold 68 also has a linear array of orifices 72 that traverse the height of the manifold 68. As further shown in FIGS. 3 and 4, each orifice defines an upper recess region 94 and a lower recess region 96. The recess regions preferably are cavities with conical-shaped exterior surfaces, however, the cavities can have any external shape. The only limitation being that the contour of each interior surface substantially matches that of the exterior surface of the protrusions of the top and lower ferrule plates as described herein. As depicted in FIG. 4, the diameter of the recess regions 94, 96 at their narrow ends are slightly less than the corresponding initial diameters of the protrusions 74, 76. This angle difference allows compressive forces to be applied onto the tip of each capillary. In a preferred embodiment, the inner surfaces of the recess regions 94, 96 define conical-shaped cavities suitably contoured to receive corresponding conical-shaped protrusions 74 of upper ferrule plate 86 and protrusions 76 of and lower ferrule plate 70, respectively. As shown in FIG. 4, recess regions 94, 96 are connected by a narrow gap 98. The height of the gap preferably ranges from 50 µm to 150 µm. Manifold 68 is preferably made of a rigid polymer material such as polyetherimide (PEI) that is that sold under the tradename ULTEM by General Electric Co., polyether ether ketone, and acetal (e.g., DELRIN).

Figure 3:
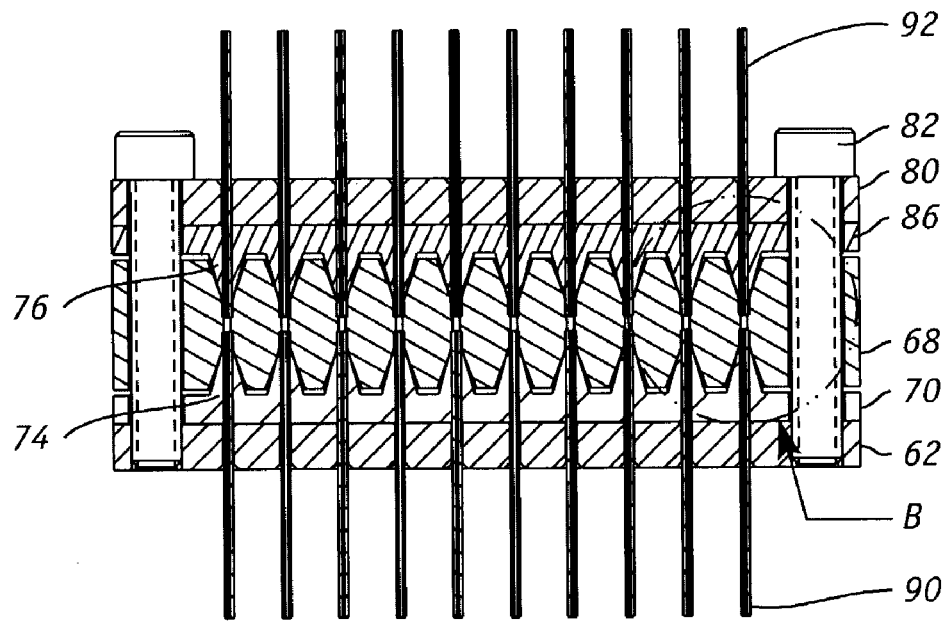
FIG. 3 is a cross-sectional view of the device as assembled.
Figure 4:
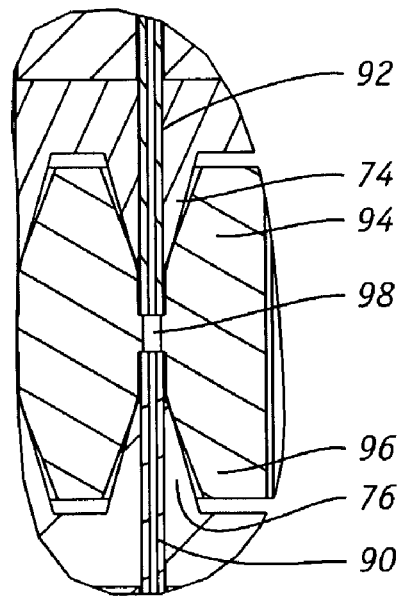
FIG. 4 is an enlarged view of portion B of the device from FIG. 3.

As shown in FIGS. 1, 3, and 4, upper ferrule plate 86, which mates with manifold 68, also has a linear array of apertures 78 on its upper surface with each aperture defining a passage which traverses the height of the upper ferrule plate. (A capillary 92 is positioned in each passage.) The upper ferrule plate 86 has an underside with an array of conical-shaped protrusions 74 projecting from the underside such that each passage (shown in FIG. 4 as being occupied by capillary 92) terminates at the end of a conical-shaped protrusion 74.

The lower ferrule plate 70 is essentially identical to the upper ferrule plate 86 but its positioned is reversed. As shown in FIGS. 1, 3, and 4 lower ferrule plate 70, which mates with manifold 68, has a linear array of apertures on its lower surface with each aperture defining a passage which traverses the height of the lower ferrule plate 70. (A capillary 90 is positioned in each passage.) The lower ferrule plate 70 has an topside with an array of conical-shaped protrusions 76 projecting therefrom such that each passage terminates at the end of a conical-shaped protrusion 76. It is preferred that the upper and lower ferrule plates 86, 70 be made of material that is both deformable under mechanical compression and that is easy to machine or mold.

While this embodiment of the connector device has been illustrated using inlet and outlet capillaries without ferrules, the capillaries can also be attached preferably using one-piece ferrules. Furthermore, vials can also be employed and the connector device can be attached directly to a microscale device as further described herein.

Mechanical compression is applied to upper and lower ferrule plates 86, 70 by means of a rigid, top interconnect plate 80 which has an array of holes 84 which are aligned to the array of apertures of the upper and lower ferrule plates 86, 70. Threaded walls 81 are drilled through the interconnect to provide passage for screws 82 that serve to exert mechanical compression on the assembly.

In operation, to connect a set of inlet capillaries 90 to a corresponding set of outlet capillaries 92, the distal ends of the internal capillaries are inserted through the passages of the lower ferrule plate 70 and the channels of the manifold 68 until the tips of the capillaries reach the lower portion of gap 98. Similarly, a set of outlet capillaries are inserted through the holes 84 of the top interconnect plate and through the passage of the upper ferrule plate 86 until their tips reach the upper portion of gap 98. In this fashion, each outlet capillary is aligned with a corresponding inlet capillary.

The screws 82 are then tightened to assemble the interconnect device. As compressive forces are applied, the conical shaped protrusions of the upper ferrule plate 86, which are preferably made of a chemically inert material that readily deforms under mechanical compression, are inserted into the mating cavities or channels 72 of manifold 68. As a result, the bottom surface of each conical shaped body deforms around the outer surface of each capillary thereby supporting and securing the outlet capillary. Deformation of the conical shaped bodies also provides a fluid tight seal. Similarly, the conical shaped bodies of the lower ferrule plate 70, which are also preferably made of a chemically inert material that readily deforms under mechanical compression, are inserted into the mating cavities or channels of manifold 68. High pressure fluids can now flow through the two sets of capillaries.

Figure 5:
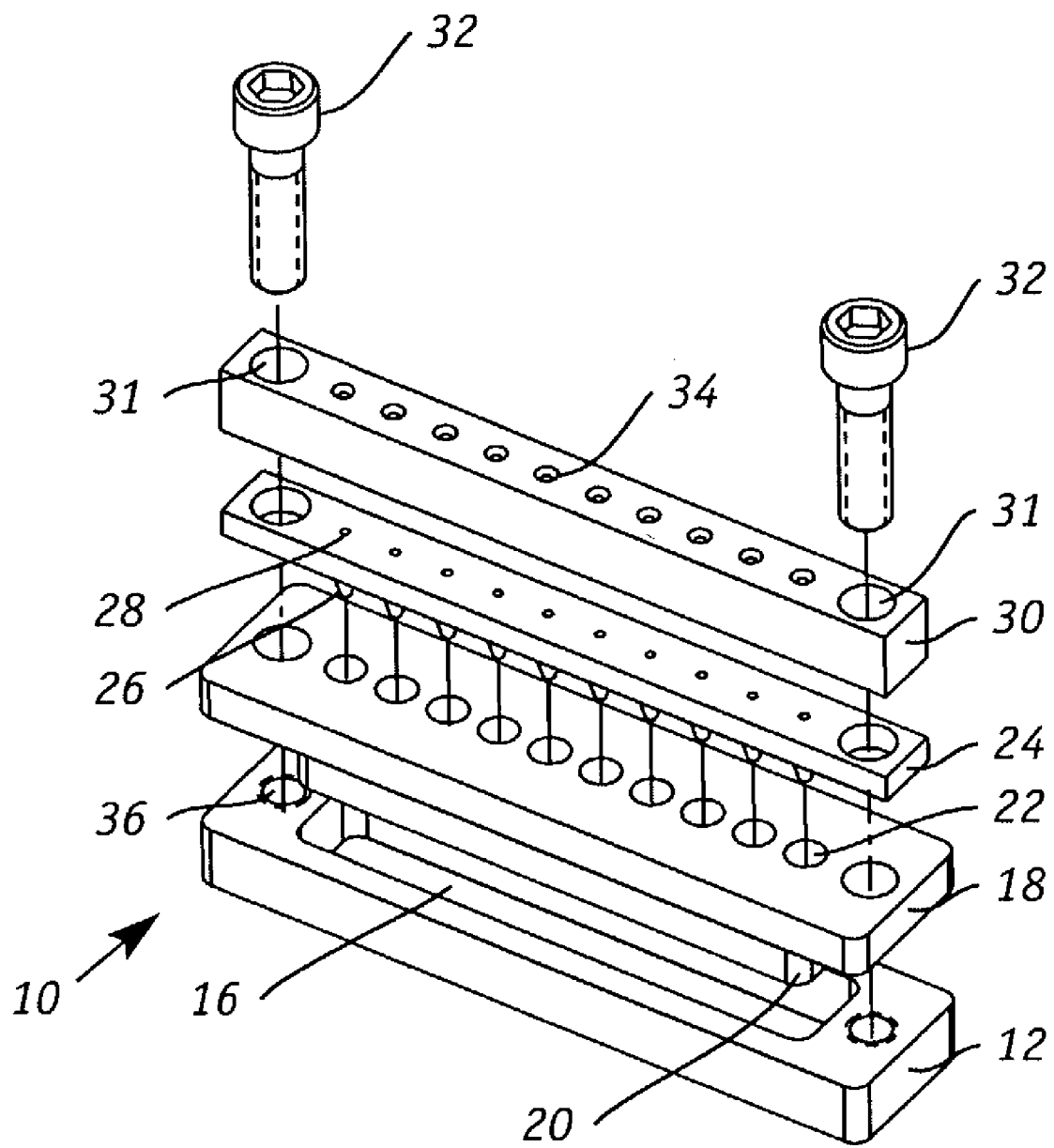
FIG. 5 is a perspective view of a second disassembled capillary to microfluidic interconnect device.
Figure 6:
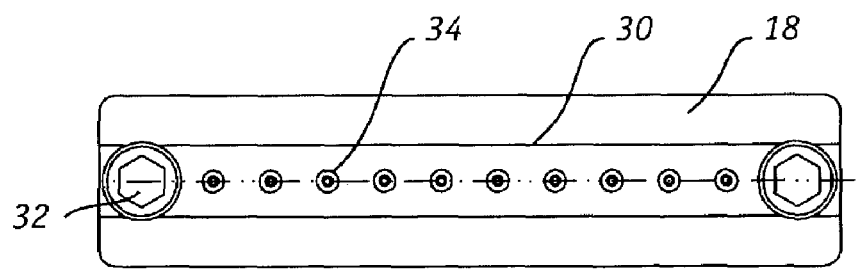
FIG. 6 is a top view of the device as assembled.

The capillary interconnect device can also be employed to connect external capillaries and/or other fluid conduits directly to the inlet and/or outlet ports of a microscale device as illustrated in FIGS. 5-8. As depicted in FIG. 5, the device 10 includes (i) a lower interconnect stiffening or support plate 12; (ii) manifold 18; (iii) ferrule plate 24; and (iv) top interconnect plate 30. The support plate 12 and top interconnect plate 30 ensure uniform sealing of device 10 as described further herein. Support plate 12 is provided with threaded wells 36 at both ends that receive screws 32 that hold the various parts of the capillary interconnect device 10 in proper orientation and that fasten the parts of the device together. Support plate 12 has an internal cavity or slot 16 that acts as a receptacle for a lower portion 20 of manifold 18. Both support plate 12 and top interconnect plate 30 are preferably made of metal, e.g., stainless steel, or high strength ceramics.

Figure 7:
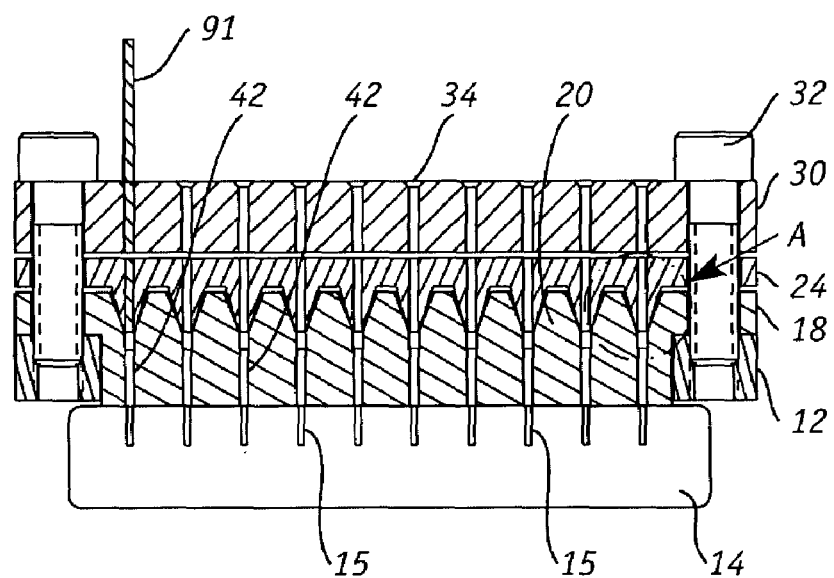
FIG. 7 is a cross-sectional view of the assembled device shown positioned on a substrate.
Figure 8:
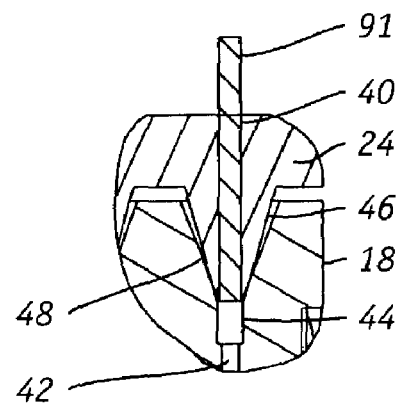
FIG. 8 is an enlarged view of portion A of the device from FIG. 7.
Figure 9:
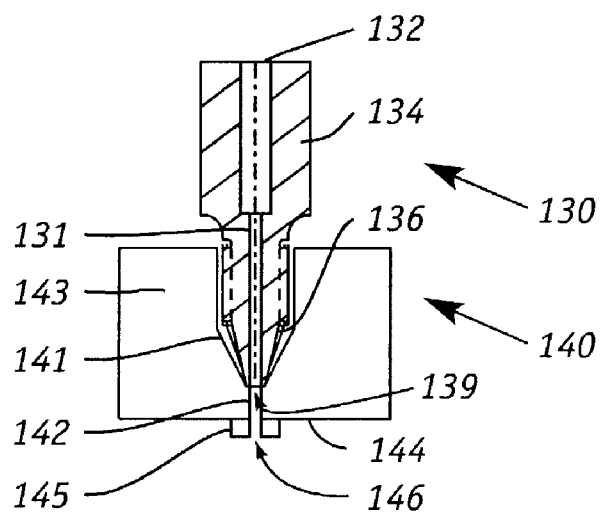
FIGS. 9-11 illustrate a one-piece ferrule.

As further shown in FIGS. 7 and 8, the lower portion 20 of manifold 18 fits into slot 16 of support plate 12 so that the lower planar surface of manifold 18 rests on the surface of substrate 14, e.g., microfluidic chip. The substrate 14 includes a number of fluid channels 15 with inlet and/or outlet ports on the substrate surface. The manifold 18 is preferably made of a polymer material that is rigid and that will adhere to glass which is the material of many conventional microscale devices. A preferred material is a polyetherimide that is that sold under the tradename ULTEM by General Electric Co. Preferably manifold 18 is bonded to substrate 14 with a suitable adhesive.

As shown in FIGS. 5 and 8, the top surface of manifold 18 has a linear array of with recess regions 22 which are preferably cavities with conical-shaped, i.e. tapered, exterior surfaces 46. It is understood that the cavities can have any shape, the only limitation being that the contour of each inner surface 48 substantially matches that of the exterior surfaces 46 of the protrusions from the ferrule plate as described herein. Preferably the two surface angles are not the same to permit enhanced deformation at the tip of the ferrule plate protrusions. As further shown in FIGS. 7 and 8, each conical-shaped cavity 22 is connected to channel sections 42, 44 that runs to the bottom surface the manifold. In this case, the diameter of the upper portion 44 of the channel is slightly larger than the remaining lower section 42.

As shown in FIGS. 5, 7, and 8, ferrule plate 24, which mates with manifold 18, also has a linear array of apertures 28 on its upper surface with each aperture defining passages 40 which traverses the height of the ferrule plate 24. The ferrule plate 24 has an underside with an array of conical shaped protrusions 26 projecting from the underside such that each passage 40 terminates at the end of a protrusion 26. It is preferred that the ferrule plate 24 be made of material that is both deformable under mechanical compression and that is easy to machine or mold. Suitable materials include, for example, polyether ether ketone, high density polyethylene, or polyamide. A preferred material is a solid, abrasion resistant, self-lubricating, polyamide available under the trade name VESPEL from Du Pont Corporation.

Mechanical compression is applied to ferrule plate 24 by means of a rigid, top interconnect plate 30 which has an array of holes 34 that are aligned to apertures 28 of ferrule plate 24. Threaded walls 31 are drilled through the interconnect plate to provide passage for screws 32 that serve to exert mechanical compression on the assembly.

As illustrated in FIG. 7, the interconnect device 10 can be employed to deliver and/or remove fluids from a microscale device 14. The device 10 as assembled is preferably attached with adhesive on the upper surface of the microscale device 14 which has inlet and outlet ports that are connected to internal channels 15. The dimensions and spacings of the ports match those of passages 42 such that the lower surface of device 10 can be attached, e.g., bonded with epoxy, directly onto the upper surface of the microscale device so that each passage 42 of device 10 will be aligned with an inlet and/or outlet port of channel 15 of microscale device 10. In this fashion, no internal capillary is needed to connect device 10 to microscale device 14, that is, passages 42 are in direct fluid communication with channels 15. Capillary 91 is depicted as being positioned within one of the passages 42.

In operation, in one embodiment, a set of external capillaries are connected by inserting their proximal ends through holes 34 of the top interconnect plate 30 and through apertures 28 of the ferrule plate 24 until their tips bottom out at the upper channel section 44 of the manifold. In this fashion, each external capillary serves as a source of fluid to the microscale device or as a conduit through which fluid is removed from the microscale device. As the screws 32 are tightened and the compressive forces applied as shown in FIG. 5, the conical-shaped protrusions 26 of ferrule plate 24, which are preferably made of a chemically inert material that readily deforms under mechanical compression, are inserted into the mating conical-shaped cavities 22 of manifold 18. As a result, as shown in FIG. 8, the bottom surface 46 of each conical-shaped protrusion deforms around the outer surface 48 of the conical-shaped cavities. Deformation of the conical-shaped protrusions also provides a fluid tight seal around the capillary to the microscale device.

Figure 10:
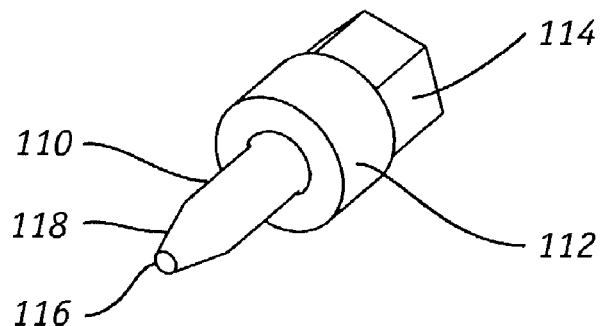
Figure 11:
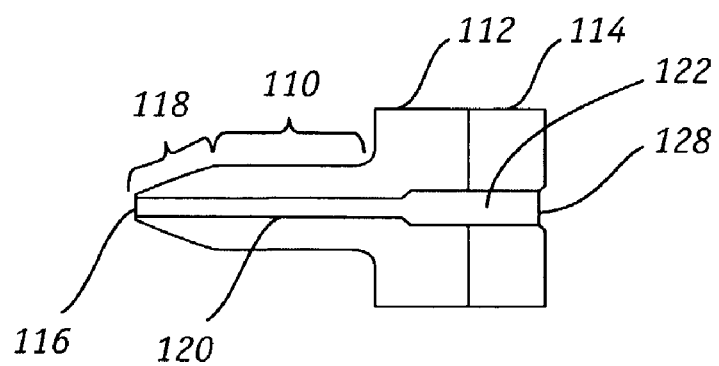

FIGS. 10 and 11 also depict the threaded, one piece ferrule. The ferrule includes an adapter body 112 having an hexagonal nut 114 on one side and an elongated member 110,118 on the other side. End portion 118 of the elongated member is tapered. The ferrule has internal bore 120,122 that runs the length of the ferrule from inlet 128 to outlet 116. Preferably, as shown in FIG. 11, the proximal portion 122 of the bore is broader to facilitate insertion of a capillary tube into the wider distal portion 120 of the bore. The wall of the bore at the tapered end will collapse directly against the tube as compressive forces are created as the ferrule is screwed into the threaded conical-shaped cavity. This effectively prevents the capillary tube from extruding during high pressure operations.

Each ferrule is machined from a block of material to fabricate a single, integral piece ferrule. The bore is formed using conventional drills and threads are machined preferably on the exterior of the non-taper portion 110 of the elongated member. When using the ferrule, no flange is needed. In addition, a mating sleeve is not needed since the bore will collapse against the tube under compressive force. By "mating sleeve" is meant an extra tube that is inserted into the bore of the ferrule before the capillary tube that will be transferring a fluid of interest is inserted through the bore of the mating sleeve. Mating sleeves having an outer diameter that matches the inner diameter of prior art ferrules are used quite often but are not needed with the inventive ferrule. Machining permits exact tolerance to be maintained to improve fittings function. Because the ferrules are fabricated by machining, that is, they are not made by molding, a wide range of materials, including plastics, ceramics, and metals, for example, can be used depending on the expected operating conditions, e.g., temperature, pressure, and type of fluids the ferrule will be exposed to. The ferrules are reusable and can be finger-tightened to provide a seal that can withstand a minimum pressure of 5,000 psi.

The ferrule is particularly suited for high pressure operations to connect capillary tubes in microfluidic applications and therefore the ferrule is dimensioned accordingly. In this regard, referring to the ferrule shown in FIG. 11, the diameter of the distal portion 120 of the bore is preferably 0.0145 in. (0.368 mm) to 0.015 in. (0.38 mm) and the diameter of the proximal portion 122 of the bore is typically 0.018 in. (0.46 mm) to 0.020 in. (0.51 mm).

While the embodiments illustrated shows a plurality of capillary interconnections oriented linearly the device can be used for a single capillary interconnection and could be equally effective in a circular orientation to interconnect capillary bundles. Moreover, the interconnect device can be used to connect at least two substrates together.

The reusable interconnecting device can be employed to provide fluid type communication between two sets of capillaries regardless of what the capillaries are ultimately connected. Typically, at least one or more of the capillaries from one set will be connected to a substrate which refers to any microfluidic device that has an integrated network of microfluidic channels disposed therein. The particular design or configuration of the internal structure of the substrate is not critical. Such substrates are also referred as microfluidic or microscale wafers or chips.

The substrate include microfluidic channels, e.g., sealed enclosed groove, depression, and tube, which is adapted to handle small volumes of fluid. Typically, the channel is a tube, channel or conduit having at least one subsection with at least one cross-sectional dimension of between about 0.1 microns and 500 microns, and typically less than 100 microns.

The substrate is preferably fabricated from glass, quartz, silicon or plastic by conventional techniques including LIGA (an acronym for the German for lithography, electroplating, and molding), deep x-ray lithography, silicon surface micromachining and lithography, electric discharge machining, and direct laser additive fabrication. In addition, commercially available substrates can be modified with appropriate dimensioned inlet and/or outlet ports as further described herein. The substrate may include reaction cells, reservoirs, and other structures that are interconnected by a network of microchannels and a series of micropumps. Such substrates are further described in U.S. Pat. No. 5,846,396 to Zanzucchi, et al. which is incorporated herein.

Conventional mechanical pumps can be employed to transport liquid fluids through the capillaries although a preferred method employs a high pressure hydraulic system that has no moving parts for converting electric potential to hydraulic force and for manipulating fluids which are described in U.S. Pat. Nos. 6,013,164 to Paul, et al., 6,019,882 to Paul, et al., 6,224,728 to Obomy, et al., and 6,277,257 to Paul, et al., and 6,290,909 to Paul, et al., which are incorporated herein by reference.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A connector assembly that provides fluid communication between first fluid-bearing conduits and second fluid-bearing conduits that comprises:
    a plurality of first fluid-bearing conduits;
    a corresponding plurality of second fluid-bearing conduits;
    a support plate;
    a manifold that is positioned on the support plate and that defines a plurality of recess regions within the manifold and having a plurality of channels wherein each channel has a first opening at a lower end of each recess region and a second opening at a lower surface of the manifold, wherein each of the second fluid-bearing conduits is positioned within one of the channels so that the distal end of each second fluid-bearing conduit is positioned in or near the first opening wherein the manifold is made of a rigid material;
    a ferrule plate that is positioned on the manifold and that defines a plurality of protrusions wherein each protrusion fits into a corresponding recess region of the manifold and the ferrule plate has a plurality of passages with each passage traversing the height of the ferrule plate and through the protrusion and wherein each of the first fluid-bearing conduits is positioned within one of the passages so that a proximal end of each first fluid-bearing conduit abuts a distal end of a corresponding second fluid-bearing conduit wherein the protrusions are made of a compliant material and wherein each recess region of the manifold has a cavity structure with a conical-shaped exterior surface and each protrusion of the ferrule plate has a corresponding conical-shaped exterior surface; and
    means for applying an axial force on the ferrule plate to case the plurality of protrusions of the ferrule plate to contact a corresponding recess region of the manifold.

2. The connector assembly of claim 1 wherein the means for applying the axial force is selected from the group consisting of a screw, cam and clamp and each of the support plate, manifold, and ferrule plate is threaded to accept the screw.

3. The connector assembly of claim 1 further comprising a top interconnect plate that is positioned on the ferrule plate wherein the means for applying an axial force engages the top interconnect plate to cause the axial force to be distributed evenly along the length of the ferrule plate.

4. The connector assembly of claim 1 wherein the top interconnect plate has a plurality of holes through which the plurality of first fluid-bearing conduits are inserted.

5. The connector assembly of claim 1 wherein the second fluid-bearing conduits are channels within a substrate wherein the channels have ports on the surface of the substrate and a lower surface of the support plate is positioned on said surface of the substrate.

6. The connector assembly of claim 5 wherein the support plate defines a slot through which a lower portion of the manifold is positioned and a lower surface of said lower portion of the manifold is attached to the substrate surface.

7. The connector assembly of claim 5 wherein the substrate is a microfluidic device.

8. The connector assembly of claim 1 wherein each of the first and second fluid-bearing conduits comprise a capillary tube with an inner diameter that ranges from 5 microns to 250 microns.

9. The connector assembly of claim 1 wherein at least one of the first fluid-bearing conduits comprises a vial.

10. The connector assembly of claim 1 wherein the plurality of first fluid-bearing conduits are arranged in a linear array along the length of the manifold.

11. The connector assembly of claim 1 wherein the plurality of first fluid-bearing conduits are arranged in a circular orientation.

12. The connector assembly of claim 1 wherein the means for applying the axial force causes the proximal end of the first fluid-bearing conduits to come into contact with the distal end of the corresponding second fluid-bearing conduits.

13. A connector assembly that provides fluid communication between first fluid-bearing conduits and second fluid-bearing conduits that comprises:
    a plurality of first fluid-bearing conduits;
    a corresponding plurality of second fluid-bearing conduits;
    a support plate;
    a lower ferrule plate that is positioned on the support plate and that defines a plurality of first protrusions;
    a manifold that is positioned on the lower ferrule plate and that defines (i) a plurality of first recess regions within the manifold and (ii) a plurality of second recess regions within the manifold, wherein each of the first recess regions is connected to a corresponding second recess region;
    an upper ferrule plate that is positioned on the manifold and that defines a plurality of second protrusions wherein each second protrusion fits into a corresponding second recess region and wherein the upper ferrule plate has a plurality of second passages with each second passage traversing the height of the upper ferrule plate and through the second protrusions, and wherein each first protrusion of the first ferrule plate fits into a corresponding first recess region so that each first passage of the lower ferrule plate is in communication with a corresponding second passage of the upper ferrule plate and wherein each of the first fluid-bearing conduits is positioned within one of first passages and each of the second fluid-bearing conduits is positioned within one of the second passages so that that a proximal end of each first fluid-bearing conduit abuts a distal end of a corresponding second fluid-bearing conduit; and
    means for applying an axial force on the first and second ferrule plates to cause the plurality first protrusions to contact a corresponding first recess region and to cause the plurality second protrusions to contact a corresponding second recess regions.

14. The connector assembly of claim 13 wherein each of the first recess regions is connected to corresponding second recess regions by channel within the manifold.

15. The connector assembly of claim 14 wherein the proximal end of each first fluid-bearing conduit and the distal end of a corresponding second fluid-bearing conduit is positioned within a channel of the manifold.

16. The connector assembly of claim 14 wherein each first recess region of the manifold has a first cavity structure with a conical-shaped exterior surface and each first protrusion of the first ferrule plate has a corresponding exterior surface with a contour that matches the conical-shaped exterior surface of the first cavity structure and wherein each second recess region of the manifold has a second cavity structure with a conical-shaped exterior surface and each second protrusion of the second ferrule plate has a corresponding exterior surface with a contour that matches the conical-shaped exterior surface of the second cavity structure.

17. The connector assembly of claim 13 wherein the means for applying the axial force comprises at least one screw and each of the support plate, manifold, and first and second ferrules is threaded to accept the screw.

18. The connector assembly of claim 13 wherein the first and second protrusions are made of a compliant material.

19. The connector assembly of claim 13 further comprising a top interconnect plate that is positioned on the upper ferrule plate wherein the means for applying an axial force engages the top interconnect plate to cause the axial force to be distributed evenly along the lengths of the upper and lower ferrule plates.

20. The connector assembly of claim 13 wherein the support plate comprises a plurality of holes through which the second fluid-bearing conduits are inserted.

21. The connector assembly of claim 19 wherein the second fluid-bearing conduits emanate from a substrate and a lower surface of the support plate is attached to a substrate surface.

22. The connector assembly of claim 21 wherein the substrate is a microfluidic device.

23. The connector assembly of claim 13 wherein at least one of the first fluid-bearing conduits comprises a vial.

24. The connector assembly of claim 13 wherein each of the first and second fluid-bearing conduits comprises a capillary tube with an inner diameter that ranges from 5 microns to 250 microns.

25. The connector assembly of claim 13 wherein the plurality of first fluid-bearing conduits are arranged in a linear array along the length of the manifold.

26. The connector assembly of claim 13 wherein the plurality of first fluid-bearing conduits are arranged in a circular array.

* * * * *